(12) United States Patent
Bonrath et al.

(10) Patent No.: US 10,005,710 B2
(45) Date of Patent: Jun. 26, 2018

(54) PROCESS OF PRODUCTION OF 1-(5,5-DIMETHYLCYCLOHEX-1-EN-1-YL)ETHANONE AND 1-(5,5-DIMETHYLCYCLOHEX-6-EN-1-YL ) ETHANONE

(71) Applicant: DSM IP ASSETS B.V., Heerlen (NL)

(72) Inventors: Werner Bonrath, Kaiseraugst (CH); Raphael Beumer, Kaiseraugst (CH); Ulla Letinois, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 15/129,948

(22) PCT Filed: Mar. 26, 2015

(86) PCT No.: PCT/EP2015/056595
§ 371 (c)(1),
(2) Date: Sep. 28, 2016

(87) PCT Pub. No.: WO2015/144832
PCT Pub. Date: Oct. 1, 2015

(65) Prior Publication Data
US 2017/0217864 A1 Aug. 3, 2017

(30) Foreign Application Priority Data
Mar. 28, 2014 (EP) .................................. 14162237

(51) Int. Cl.
*C07C 45/00* (2006.01)
*B01J 31/00* (2006.01)
*C07C 45/51* (2006.01)
*B01J 31/24* (2006.01)

(52) U.S. Cl.
CPC .......... *C07C 45/512* (2013.01); *B01J 31/2404* (2013.01); *B01J 2531/18* (2013.01)

(58) Field of Classification Search
CPC .......................... C07C 45/512; B01J 31/2404
See application file for complete search history.

(56) References Cited

U.S. PATENT DOCUMENTS

| 4,147,672 A | 4/1979 | Schulte-Elte et al. |
| 2012/0190811 A1 | 7/2012 | Postma et al. |

FOREIGN PATENT DOCUMENTS

| CN | 102300838 | 12/2011 |
| CN | 102397794 | 4/2012 |
| WO | WO 2004/050602 | 6/2004 |
| WO | WO 2010/043522 | 4/2010 |

OTHER PUBLICATIONS

Lu et al. Gold (I) and Bronsted Acid Catalyzed Intramolecular Rearrangements of Vlnylidenecyclopropanes. Chemistry and European Journal, 2010, vol. 16, 10975-10979.*
International Search Report for PCT/EP2015/056595 dated Jun. 5, 2015, 3 pages.
Kraft et al., "Synthesis and Odor of Aliphatic Musks: Discovery of a New Class of Odorants", *European Journal of Organic Chemistry*, vol. 2004, No. 2, Jan. 2004, pp. 354-365.
Cadierno et al., "Isomerization of Propargylic Alcohols into [alpha], [beta]-Unsaturated Carbonyl Compounds Catalyzed by the Sixteen-Electron Allyl-Ruthenium(II) Complex [Ru([eta]3-2-C3H4Me) (CO) (dppf)] [SbF6]", *Advanced Synthesis & Catalysts*, vol. 348, No. 1-2, Jan. 2006, pp. 101-110.
Chang et al., "Additive-assisted Rupe rearrangement of 1-ethynlycyclohexan-1-ol in near-critical water", *Chemical Papers*, vol. 66, No. 1, Oct. 7, 2011, pp. 33-38.
Engel et al., "The Meyer-Schuster rearrangement for the synthesis of [alpha], [beta]-unsaturated carbonyl compounds", *Organic & Biomolecular Chemistry*, vol. 7, No. 20, Jan. 2009, 10 pages.

* cited by examiner

*Primary Examiner* — Sikarl A Witherspoon
(74) *Attorney, Agent, or Firm* — Nixon & Vanderhye P.C.

(57) ABSTRACT

The present invention relates to an improved method for producing of 1-(5,5-dimethylcyclohex-1-en-1-yl)ethanone and 1-(5,5-dimethylcyclohex-6-en-1-yl)ethanone.

11 Claims, No Drawings

PROCESS OF PRODUCTION OF 1-(5,5-DIMETHYLCYCLOHEX-1-EN-1-YL)ETHANONE AND 1-(5,5-DIMETHYLCYCLOHEX-6-EN-1-YL)ETHANONE

This application is the U.S. national phase of International Application No. PCT/EP2015/056595 filed 26 Mar. 2015 which designated the U.S. and claims priority to EP Patent Application No. 14162237.3 filed 28 Mar. 2014, the entire contents of each of which are hereby incorporated by reference.

The present invention relates to an improved method for producing 1-(5,5-dimethylcyclohex-1-en-1-yl)ethanone and 1-(5,5-dimethylcyclohex-6-en-1-yl)ethanone.

1-(5,5-dimethylcyclohex-1-en-1-yl)ethanone (compound of formula (I′)) and 1-(5,5-dimethylcyclohex-6-en-1-yl)ethanone (compound of formula (I″))

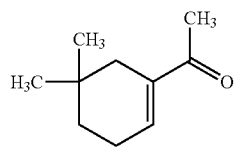

(I′)

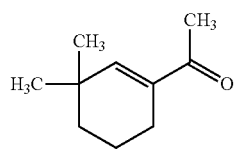

(I″)

are versatile and important intermediates for the synthesis of various known fragrance compounds.

In the context of the present patent application the compounds of formula (I′) and of formula (I″) are summarized by the following formula (I)

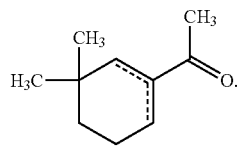

(I)

Compounds of formula (I) (which means either the compound of formula (I′) or the compound of formula (I″) as such as well as any mixture of these two compounds) can be used to produce for example the following compounds of formulae (Ia) to (Ig):

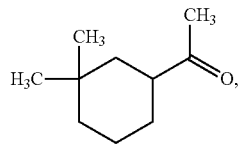

(Ia)

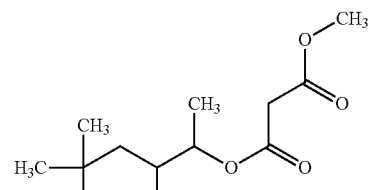

(Ib)

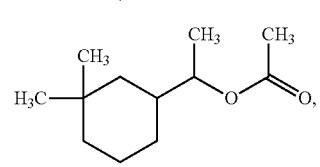

(Ic)

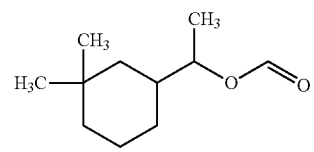

(Id)

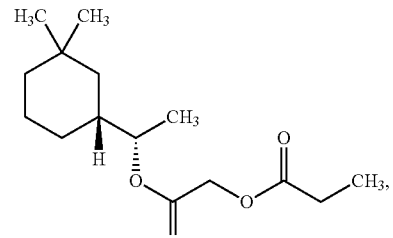

(Ie)

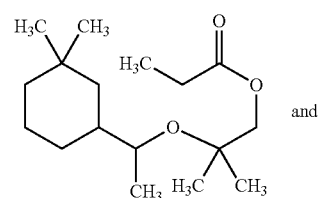

(If) and

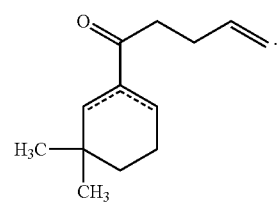

(Ig)

All these reactions to obtain the compounds of formula (Ia) to (Ig) from the compound of formula (I) are well known from the prior art.

The compounds of formula (I) are usually produced by using formic acid (HCOOH) as a catalyst in the rearrangement of compounds having formula (II)

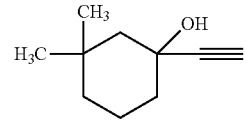

(II)

This reaction is described for example in U.S. Pat. No. 4,147,672.

This method of production by using strong Bronsted acids under corrosive reaction conditions does cause some problems.

For example it is necessary to use expensive acid-resistant equipment for the production. Furthermore the handling of corrosive compounds is not easy for the production team.

Due to the importance of the compounds of formula (I), there is always a need for finding an improved method of production of the compounds of formula (I).

Surprisingly it was found that it possible to produce the compounds of formula (I) by a gold catalyzed Rupe-Kambli rearrangement.

Therefore the present invention relates to a process (A) of production of the compounds of formula (I)

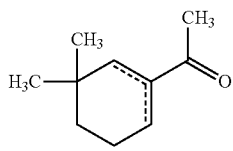
(I)

by a rearrangement reaction of the compound of formula (II)

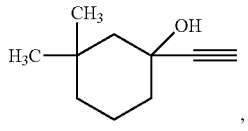
(II)

wherein the rearrangement reaction is catalyzed in the presence of at least one Au(I)-complex.

A further problem, which occurs when synthesizing the compounds of formula (I) is that there are competitive reactions occurring, such as the Meyer Schuster rearrangement:

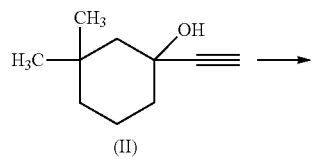
(II)

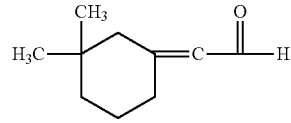

By the use of the gold catalyst the above mentioned side reaction (which does not lead to the compounds of formula (I)) is (more or less) suppressed, which means that the yield and conversion of the new process according to the present invention are excellent.

Especially the following Au(I)-complexes are used as catalysts for the process according to the present invention:

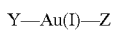
Y—Au(I)—Z    (III).

wherein

Z is an anion, which is selected from the group consisting of $[BX_4]^-$, $[PX_6]^-$, $[SbF_6]^-$, $[ClO_4]^-$, $CF_3COO^-$, sulfonates, tetra(3,5-bis(trifluoromethyl)phenyl)borate ($BAr_F^-$), tetraphenylborate, and the anion of formula (IV);

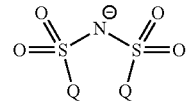
(IV)

wherein Q represents a phenyl or a $C_{1-8}$-alkyl which preferably is substituted by at least one substituent chosen from the group consisting of F, Cl, $NO_2$ and X is a halogen atom, especially F and Cl, and Y is an organic ligand.

Therefore the present invention also relates to process (B), which is the process (A), wherein at least one Au(I) complex of the following compound of formula (III)

Y—Au(I)—Z    (III), wherein

Z is an anion, which is selected from the group consisting of $[BX_4]^-$, $[PX_6]^-$, $[SbF_6]^-$, $[ClO_4]^-$, $CF_3COO^-$, sulfonates, tetra(3,5-bis(trifluoromethyl)phenyl)borate ($BAr_F^-$), tetraphenylborate, and the anion of formula (IV)

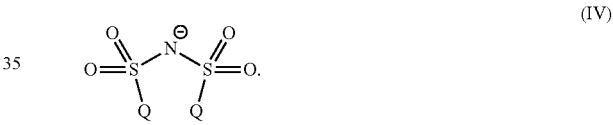
(IV)

wherein Q represents a phenyl or a $C_{1-8}$-alkyl group which preferably is substituted by at least one halogen atom, and X is a halogen atom, especially F and Cl, and Y is an organic ligand, is used.

Preferably Y is an organic ligand selected from the group consisting of following ligands ($Y^1$) to ($Y^{10}$):

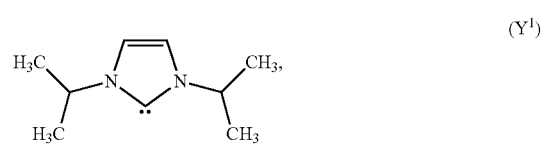
($Y^1$)

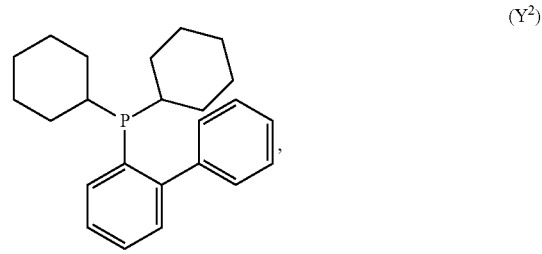
($Y^2$)

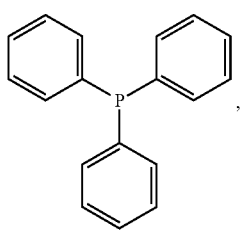  (Y³),
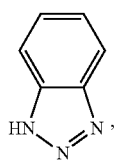  (Y⁴)
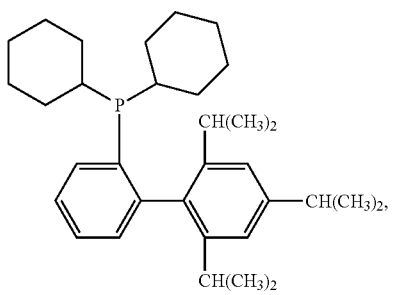  (Y⁵)
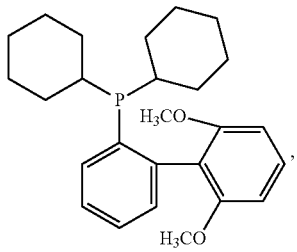  (Y⁶)
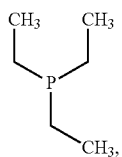  (Y⁷)
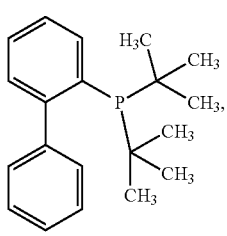  (Y⁸)
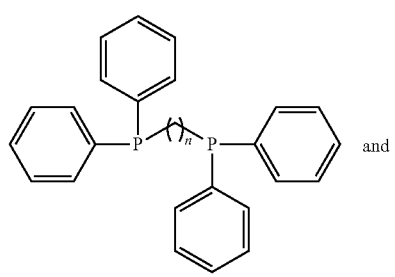  (Y⁹)
n = 1-6
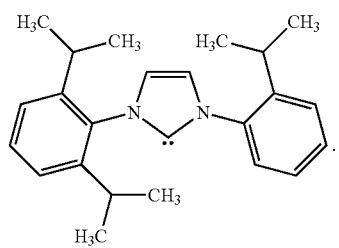  (Y¹⁰)
Therefore the present invention also relates to process (C), which is the process (A) or (B), wherein the organic ligand Y of Au(I) complex of formula (III) is selected from the group consisting of following ligands (Y¹) to (Y¹⁰):
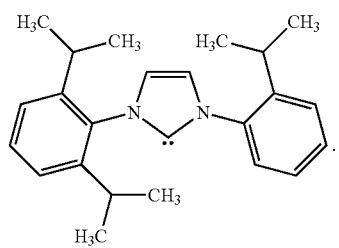  (Y¹)
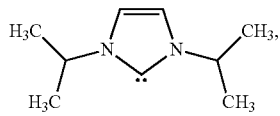  (Y²)
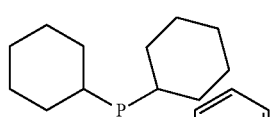  (Y³)
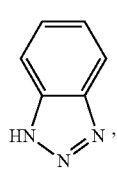  (Y⁴)

-continued (Y⁵)
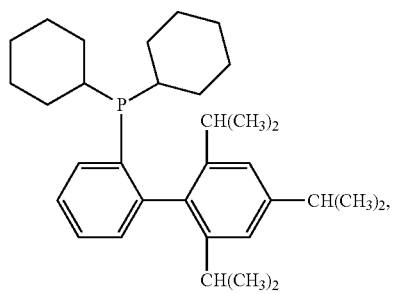

(Y⁶)
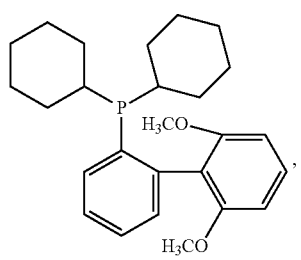

(Y⁷)
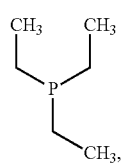

(Y⁸)
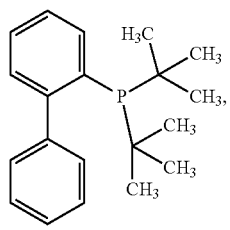

(Y⁹)
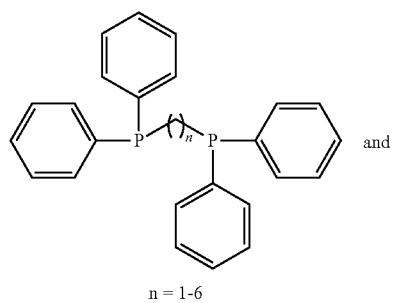
and n = 1-6

(Y¹⁰)
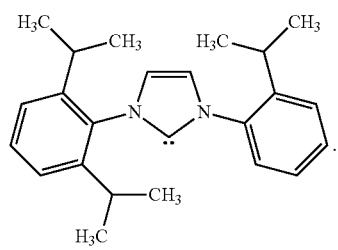

Preferably Z is an anion selected from the group consisting of following anions $[BF_4]^-$, $[PF_6]^-$, $[SbF_6]^-$, $[ClO_4]^-$, $CF_3COO^-$, sulfonates (such as triflate $CF_3SO_3^-$), tetra(3,5-bis(trifluoromethyl)phenyl)borate ($BAr_F^-$), tetraphenylborate, and the anion of formula (IV')

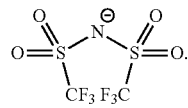 (IV')

Therefore the present invention also relates to process (D), which is the process (A), (B) or (C), wherein the anion Z is selected from the group consisting of following anions $[BF_4]^-$, $[PF_6]^-$, $[SbF_6]^-$, $[ClO_4]^-$, $CF_3COO^-$, sulfonates (such as triflate $CF_3SO_3^-$), tetra(3,5-bis(trifluoromethyl)phenyl)borate ($BAr_F^-$), tetraphenylborate, and the anion of formula (IV')

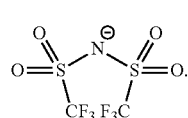 (IV')

The catalyst (the Au(I) complex) can be added to the reaction mixture in the form, which is defined by formula (I), but it is also possible that the Au(I)-complex is formed in situ in the reaction mixture (before the starting material is added or after the starting material is added).

For example it is possible to add the organic ligand in the form of a salt (such as for example a chloride: Y—Au(I)Cl) and the anion in form of a metal salt (such for example a silver salt Ag(I)Z). The Au(I) complex is then formed in situ and the resulting metal salt (for example AgCl) does not interfere negatively.

Therefore the present invention relates to a process (E), which is the process (A), (B), (C) or (D), wherein the Au(I) complex is added to reaction mixture as such.

Furthermore the present invention relates to a process (F), which is the process (A), (B), (C), (D) or (E), wherein the Au(I) complex is formed in situ in the reaction mixture.

Preferred Au(I) complexes of formula (III) are the following ones.

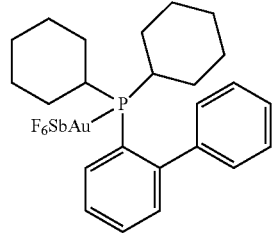 (III')

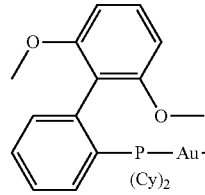 (III")

and

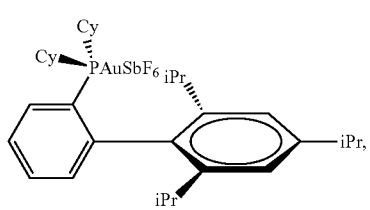

(III''')

wherein Cy is cyclohexyl, iPr is isopropyl and Tf is triflate.

Therefore a preferred process relates to a process as described above wherein at least one complex of formula (III'), (III'') and/or (III''') is used.

The process according to the present invention is usually carried out in a solvent (or a mixture of solvents). Suitable solvents are aliphatic hydrocarbons, alcohols. Preferred solvents are alcohols, such as methanol, ethanol, 2-butanol and tert-butanol.

Therefore the present invention also relates to a process (G), which is the process (A), (B), (C), (D), (E) or (F), wherein the process is carried out in a solvent or a mixture of solvents.

Furthermore the present invention relates to a process (G'), which is process (G) wherein the solvent is chosen from the group consisting of methanol, ethanol, 2-butanol and tert-butanol.

The process according to the present invention is usually carried out at elevated temperature, usually 30° C.-120° C. A preferred reaction temperature is between 40° C. and 110° C., more preferred between 50° C. and 100° C.

Therefore the present invention also relates to a process (H), which is the process (A), (B), (C), (D), (E), (F), (G) or (G'), wherein the process is carried out at elevated temperature.

Therefore the present invention also relates to a process (H'), which is the process (H), wherein the process is carried out at a temperature from 30° C. to 120° C.

Therefore the present invention also relates to a process (H''), which is the process (H), wherein the process is carried out at a temperature from 40° C. to 110° C.

Therefore the present invention also relates to a process (H'''), which is the process (H), wherein the process is carried out at a temperature from 50° C. to 100° C.

Usually the Au(I) complex is present in an amount, wherein the substrate (compound of formula (II)) to catalyst ratio is 2:1 to 10000:1, preferred are 10:1 to 3000:1.

Therefore the present invention also relates to a process (I), which is the process (A), (B), (C), (D), (E), (F), (G), (G'), (H), (H'), (H'') or (H'''), wherein the substrate (compound of formula (II)) to catalyst ratio is 2:1 to 10000:1, preferably 10:1 to 3000:1.

The reaction time of the process (to obtain the desired product in reasonable amount) according to the present invention is usually 60 minutes to 300 minutes.

As stated above the compounds of formula (I) can be used as starting material to the synthesis of other organic compounds (especially the ones of formulae (Ia)-(Ig)).

The following examples serve to illustrate the invention. If not otherwise stated the temperature is given in degree Celsius and all parts are related to the weight.

EXAMPLES

Example 1: Rearrangement of 1-ethynyl-3,3-dimethylcyclohexanol

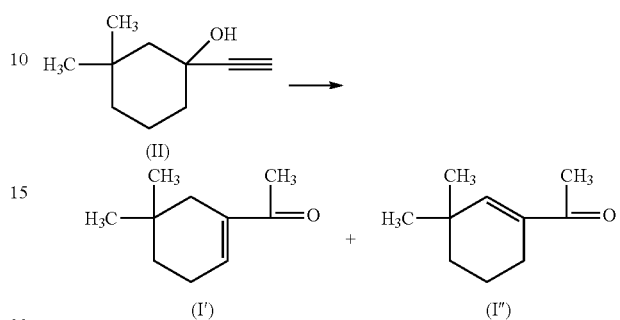

118.8 mg (0.2 mmol, 0.1 equiv.) of dicyclohexylphosphine biphenyl gold(I)-chloride and 56.88 mg (0.2 mmol, 0.1 equiv.) of silver triflate were dissolved under argon at 23° C. in 5.0 ml of tert-butanol in a septum bottle. 362.6 µl (90%, 2 mmol, 1 equiv.) of 1-ethynyl-3,3-dimethylcyclohexanol (90%, 2 mmol, 1 equiv.) were added. The reaction mixture was stirred for 105 min at 80° C. Afterwards the reaction mixture was cooled to 23° C. A sample was taken out and analyzed by GC and NMR.

The conversion of this reaction was 98.9%. The products of formulae (I' and I'') were obtained in a yield of 89.6 wt-%.

It is possible to separate the two isomers if desired.

Examples 2-6

The following examples were carried out under the same reaction condition as in example 1.

The ligands are defined as above and the ligands are added in the chloride form and the anions in the form of the Ag(I) salt.

| Exp. | ligand | anion | conversion [%] | yield [%] |
|---|---|---|---|---|
| 2 | $Y^2$ | $SbF_6^-$ | 98.6 | 78.3 |
| 3 | $Y^2$ | $O=S(=O)(CF_3)O^{\ominus}$ | 95.4 | 88.9 |
| 4 | $Y^2$ | $(O=S(=O)CF_3)_2N^{\ominus}$ | 98.7 | 89.1 |
| 5 | $Y^3$ | $BF_4^-$ | 78.5 | 40.8 |
| 6 | $Y^3$ | $O=S(=O)(CF_3)O^{\ominus}$ | 75.6 | 41.9 |

Comparative Examples (Examples 7-11)

The same reaction as described in Example 1 was repeated, but Au catalysts, which do not fall under the scope of the claims were used.

Example 7 and 8 are carried out without any organic ligands. AuCl was used in combination with the silver salt

| Exp. | ligand | anion | conversion [%] | yield [%] |
|---|---|---|---|---|
| 7 | — | BF4—[−] | 16.8 | 0 |
| 8 | — | 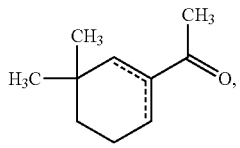 | 5.3 | 3.1 |

Example 9, 10 and 11 and 8 are carried out with catalysts where Au(0) is adsorbed on a carrier.

| Exp. | Cat | conversion [%] | yield [%] |
|---|---|---|---|
| 9 | Au/TiO$_2$ | 2.9 | 0 |
| 10 | Au/Al$_2$O$_3$ | 4.8 | 0 |
| 11 | Au/C | 4.6 | 0 |

Therefore it can be seen that the choice of the suitable (claimed) catalyst is essential.

The invention claimed is:

1. A process for producing compounds of formula (I):

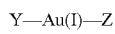

(I)

wherein
the process comprises conducting a catalyzed rearrangement reaction at an elevated temperature of 30° C. to 120° C. of a compound of formula (II):

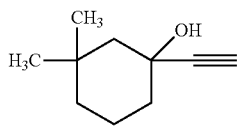

(II)

wherein
the rearrangement reaction is catalyzed by at least one Au(I)-complex.

2. The process according to claim 1, wherein the at least one Au(I) complex is a compound of formula (III):

$$Y-Au(I)-Z \quad (III),$$

wherein
Z is an anion which is selected from the group consisting of [BX$_4$]$^-$, [PX$_6$]$^-$, [SbF$_6$]$^-$, [ClO$_4$]$^-$, CF$_3$COO$^-$, sulfonates, tetra(3,5-bis(trifluoromethyl) phenyl)borate (BAr$_F^-$), tetraphenylborate, and an anion of formula (IV):

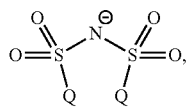

(IV)

wherein
Q represents a phenyl or a C$_{1-8}$-alkyl;
X is a halogen atom, and
Y is an organic ligand.

3. The process according to claim 2, wherein the organic ligand Y of the Au(I) complex of formula (III) is selected from the group consisting of:

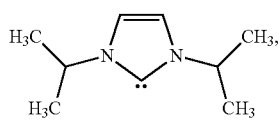

(Y$^1$)

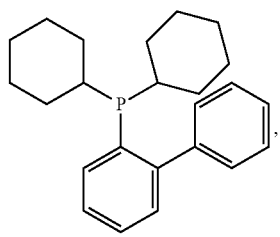

(Y$^2$)

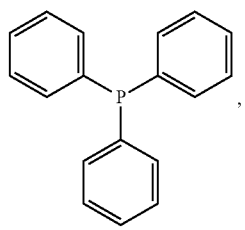

(Y$^3$)

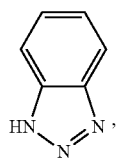

(Y$^4$)

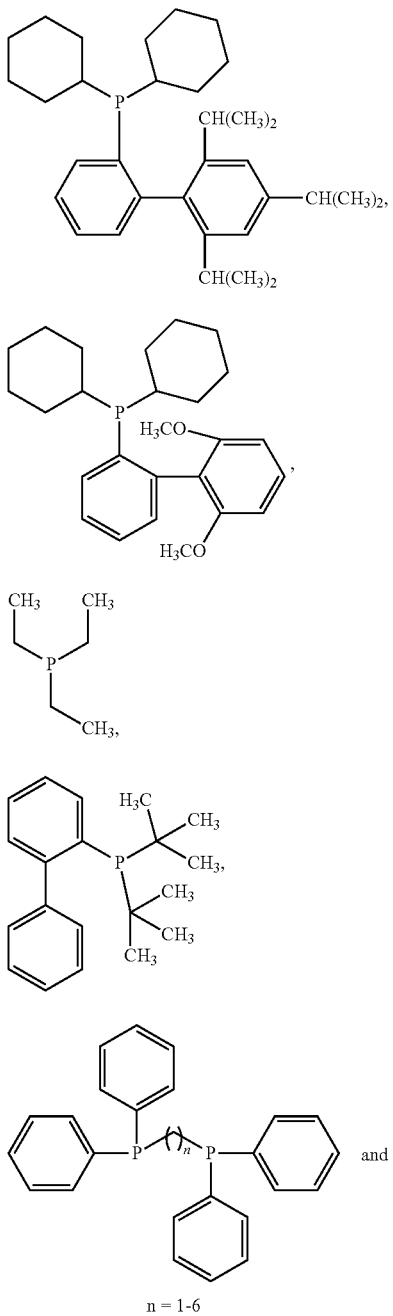

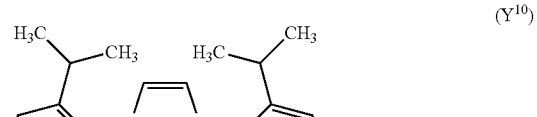

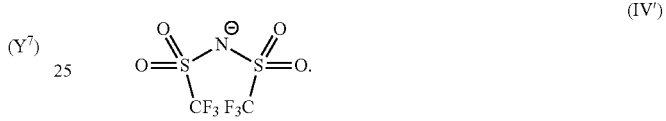

4. The process according to claim 2, wherein the anion Z of the Au(I) complex of formula (III) is an ion selected from the group consisting of $[BF_4]^-$, $[PF_6]^-$, $[SbF_6]^-$, $[ClO_4]^-$, $CF_3COO^-$, sulfonates, tetra(3,5-bis(trifluoromethyl)phenyl)borate ($BAr_F^-$), tetraphenylborate, and the anion of formula (IV'):

(IV')

5. The process according to claim 1, wherein the process is carried out in a solvent or a mixture of solvents.

6. The process according to claim 5, wherein the solvent is selected from the group consisting of methanol, ethanol, 2-butanol and tert-butanol.

7. The process according to claim 1, wherein Au(I)-complex is used in an amount to provide a ratio of the compound of formula (II) to catalyst which is from 2:1 to 10000:1.

8. The process according to claim 2, wherein Q represents a $C_{1-8}$-alkyl which is substituted by at least one substituent selected from the group consisting of F, Cl and $NO_2$.

9. The process according to claim 2, wherein X represents F or Cl.

10. The process according to claim 1, wherein the catalyzed rearrangement reaction is carried out at an elevated temperature of 40° C. to 110° C.

11. The process according to claim 1, wherein the catalyzed rearrangement reaction is carried out at an elevated temperature of 50° C. to 100° C.

* * * * *